United States Patent
Kaplan et al.

(10) Patent No.: US 7,030,272 B2
(45) Date of Patent: Apr. 18, 2006

(54) β-HYDROXYALKYLAMIDES PROCESS FOR THEIR PRODUCTION AND THEIR USE

(76) Inventors: Andreas Kaplan, Wiesentalstrasse 29, CH-7000 Chur (CH); René Gisler, Suesswinkelgasse 20, CH-7000 Chur (CH)

( * ) Notice: Subject to any disclaimer, the term of this patent is extended or adjusted under 35 U.S.C. 154(b) by 0 days.

(21) Appl. No.: 10/866,979

(22) Filed: Jun. 12, 2004

(65) Prior Publication Data
US 2004/0260123 A1 Dec. 23, 2004

Related U.S. Application Data

(62) Division of application No. 09/909,573, filed on Jul. 20, 2001, now abandoned.

(30) Foreign Application Priority Data
Oct. 26, 2000 (DE) .................................. 100 53 194

(51) Int. Cl.
*C07C 233/65* (2006.01)
(52) U.S. Cl. ..................... 564/186; 564/182; 564/184
(58) Field of Classification Search ................ 564/182, 564/184, 186
See application file for complete search history.

(56) References Cited

U.S. PATENT DOCUMENTS 3,932,324 A * 1/1976 Stretanski .................... 524/223
5,101,073 A * 3/1992 Schlaefer ..................... 564/137

* cited by examiner

*Primary Examiner*—Shailendra Kumar
(74) *Attorney, Agent, or Firm*—Marshall & Melhorn, LLC

(57) ABSTRACT

This invention relates to a β-hydroxyalkylamide having the general Formula I:

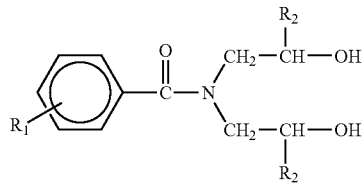

where $R_1$ is H or a linear or branched $C_1$ to $C_{10}$ alkyl and $R_2$ is a linear or branched C1 to $C_5$ alkyl.

3 Claims, No Drawings

β-HYDROXYALKYLAMIDES PROCESS FOR THEIR PRODUCTION AND THEIR USE

CONTINUING APPLICATION DATA

This application is a divisional application of U.S. patent application Ser. No. 09/909,573, which has a filing date of Jul. 20, 2001, now abandoned. U.S. patent application Ser. No. 09/909,573 was pending as of the filing date of the present application. This application claims divisional status from U.S. patent application Ser. No. 09/909,573 under 35 USC §120 and 35 USC §365(c). U.S. patent application Ser. No. 09/909,573 is hereby incorporated by reference as if set forth in its entirety herein.

BACKGROUND OF THE INVENTION

This invention relates to novel β-hydroxyalkylamides, a method for their production and their use.

β-hydroxyalkylamides are very important as intermediate products and as cross linkers for polymers. β-hydroxyalkylamides are conventionally produced by the amionlysis of alkyl esters with β-alkanol amines in the presence of basic catalysts. The β-hydroxyalkylamides are isolated and purified either by crystallization in a solvent or, especially with solid β-hydroxyalkylamides, without the use of solvent in a slurry process. A process of the above referenced type is described in U.S. Pat. No. 5,101,073 and in EP 0 473 380 B1. The slurry process is based on the fact that the equilibrium reaction that occurs during the production of the β-hydroxyalkylamides is shifted toward the desired end product as a result of the fact that the desired β-hydroxyalkylamide is precipitated from the melt by tempering in a defined temperature range and the melt is then crystallized. A disadvantage of this method is the use of equimolar quantities of alkyl ester and β-hydroxyalkylamide.

An additional process for the production of β-hydroxyalkylamides is described in DE 198 23 925. In this method, the ester is converted without the use of solvents with the alkanol amines in the presence of basic catalysts.

EP-A-322 834 describes a powder coating which contains a polyester and β-hydroxyalkylkamides as cross linkers (curing agents). Corresponding coatings with good characteristics can be produced with the formulation described in said document.

On account of the major importance of β-hydroxyalkylamides as an intermediate product, especially as cross linkers for polyester powder coats as disclosed EP-A-322 834, there has recently been a great deal of interest in new and innovative β-hydroxyalkylamides.

On the basis of the prior art described above, the object of this invention is to propose new, previously unknown β-hydroxyalkylamides and a corresponding process for their production.

The invention teaches that this object can be accomplished with regard to the β-hydroxyalkylamides by utilizing a β-hydroxyalkylamide having the general Formula I:

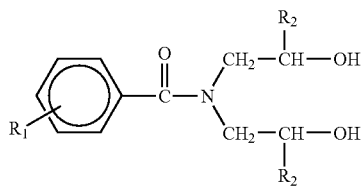

wherein $R_1$ is H or a linear or branched $C_1$ to $C_{10}$ alkyl and $R_2$ is a linear or branched $C_1$ to $C_5$ alkyl to cross-link a polymer.

The β-hydroxyalkylamide claimed by the invention is defined by the general Formula I.

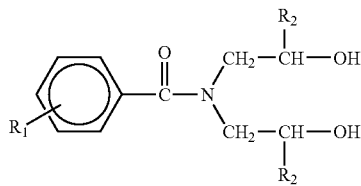

In Formula I, $R_1$ stands for hydrogen or a linear or branched $C_1$ to $C_{10}$ alkyl. $R_2$ is a linear or branched $C_1$ to $C_5$ alkyl. The β-hydroxyalkylamides claimed by the invention are characterized in particular by the substituted carbon atom next to the OH group. In the β-hydroxyalkylamides claimed by the invention, the $R_2$ group is located here.

The β-hydroxyalkylamide is preferably constructed so that the $R_1$ group is H, tert-butyl, isopropyl or pentyl and is located in the para position to the CO group.

One particularly advantageous realization of the invention is characterized by the fact that the $R_1$ group is hydrogen and the $R_2$ group is methyl.

These β-hydroxyalkylamides are produced by converting a carboxylic acid derivative having the general Formula II.

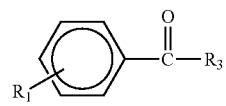

II with an alkanol amine having the general Formula III.

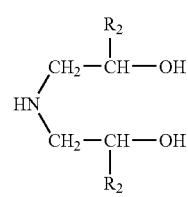

III

The $R_1$ and $R_2$ groups thereby have the definitions presented above. The $R_3$ group can thereby be a halogen, preferably chlorine, or an $OR_4$ group. If there is an $OR_4$ group, $R_4$ is a linear $C_1$ to $C_5$ alkyl, preferably a —$CH_3$ group.

The conversion of the carboxylic acid derivative and the alkanol amine preferably takes place in a solution. Preferred solvents include but are not restricted to: aromatic hydrocarbons such as benzene, toluene or xylene. Ethers such as diethylether or mixtures of the solvents listed above are also suitable.

An essential feature of the process claimed by the invention is that the carboxylic acid derivative having the general Formula II and the alkanol amine having the general Formula III are reacted with vigorous agitation of stirring. The alkanol amine is thereby preferably presented first and the carboxylic acid derivative is then added by drops with vigorous agitation of stirring.

For the case of the carboxylic acid halide, the conversion takes place at −10 to 25° C., preferably at 0 to 10° C. The reaction time is normally 0.5 to 5 hours. A reaction time of 2 hours is most advantageous.

If esters are included in the process ($R_3=OR_4$), the reaction temperature at RT is up to 150° C.

The β-hydroxyalkylamide is particularly well suited as a cross linker for polymers. β-hydroxyalkylamide is particularly preferred as a cross-linker for powder coats with polyesters or acrylates as the polymer.

Basically, the β-hydroxyalkylamide can be used as a cross linker (curing agent) analogous to the β-hydroxyalkylamides cited in EP-A-322 A34. The β-hydroxyalkylamides taught by the invention can also be used in combination with other curing agents. One example of this usage is the curing agent sold under the name PRIMID® by EMS-CHEMIE AG, Domat/Ems. PRIMID® is N,N,N',N' 2-hydroxyethyla-dipamide.

The invention is explained in greater detail below with reference to one example of production for the preferred embodiment of the invention, in which $R_1$ is H and $R_2$ is $CH_3$.

PRODUCTION EXAMPLE 44.16 g (0.32 mol) of non-aqueous $K_2CO_3$, 42.56 g (0.32 mol) of diisopropanol amine, 160 ml of water and 160 ml of diethylether are placed in a 1-liter four-necked round flask with agitator, funnel, thermometer and reflux cooler. Using the funnel, 44.96 g (0.32 mol) of benzoyl chloride are added and dissolved in 160 ml toluene. This solution is then added in drops to the reaction flask over 2 hours with vigorous agitation or stirring. During the addition, the temperature of the reaction mixture is held between 0 and 5° C. After the addition, the agitation is continued for another 30 minutes at 0 to 5° C. Then the ice bath is removed and the mixture is agitated or stirred for another 50 minutes at room temperature.

The precipitate that forms during the reaction is filtered out, washed twice with 35 ml of toluene and then three times with 30 ml of diethyl ether and then dried at 50° C. in a vacuum. The dried raw product (74.28 g) is boiled in benzene (25% solution), the isoluble portions are filtered out and the product is crystallized at room temperature. After filtration and drying, 51.80 g (68%) of N,N-Bis-(2-hydroxy-isopropyl)-benzamide is obtained with a melting point of 103° C.

Elementary Analysis: Calculated for $C_{13}H_{19}NO_3$: C=65.82%, H=8.02%, N=5.91%, O=20.25%. Found: C=66.25%, H=8.09%, N=5.83%, O=19.83%.

What is claimed is:

1. A method of utilizing a β-hydroxyalkylamide having the general Formula I:

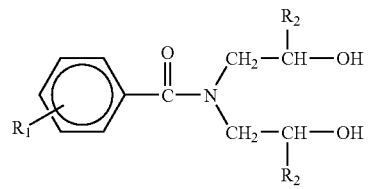

wherein $R_1$ is H and $R_2$ is $CH_3$ to cross-link a polymer.

2. The method according to claim 1 wherein the β-hydroxyalkylamide is made from a process comprising reacting a carboxylic acid derivative having the general Formula II:

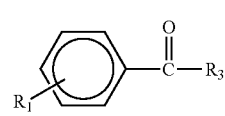

where $R_3$ is halogen or $OR_4$, whereby $R_4$ stands for a linear $C_1$ to $C_5$ alkyl, with an alkanol amine having the general Formula III:

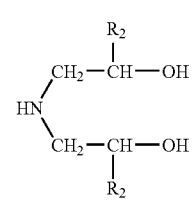

and where $R_1$ and $R_2$ are defined as indicated above.

3. The method according to claim 1, comprising mixing the β-hydroxyalkylamide with additional β-hydroxyalkylamides and/or epoxies as cross-linkers.

* * * * *